United States Patent [19]

Krespan

[11] 4,304,927
[45] Dec. 8, 1981

[54] CARBOXYLIC ACIDS, ESTERS AND SALTS OF POLYFLUOROACETONE

[75] Inventor: Carl G. Krespan, Wilmington, Del.

[73] Assignee: E. I. DuPont de Nemours and Company, Wilmington, Del.

[21] Appl. No.: 850,593

[22] Filed: Nov. 11, 1977

[51] Int. Cl.³ .................... C07C 69/716; C07C 67/00; C07C 59/347; C07C 51/09
[52] U.S. Cl. ............................... 560/176; 260/456 F; 260/501.15; 526/247; 560/180; 560/181; 560/184; 562/527; 562/537; 562/578; 568/397; 568/404; 568/599; 568/600
[58] Field of Search .................... 560/176; 260/537 S, 260/501.15; 562/527, 537, 578

[56] References Cited

U.S. PATENT DOCUMENTS 2,824,888  2/1958  Radsch ................................ 560/176
2,988,537  6/1961  Wiley .................................. 560/176
3,240,811  3/1966  Dripdale ............................. 560/176

OTHER PUBLICATIONS

J. Fluorine Chem., 3, 67 (1973).
Simmons et al., J.A.C.S., 82, pp. 2288-2296 (1960).
Banks, Fluorocarbons and their Derivatives, 1970, p. 91.

*Primary Examiner*—Vivian Garner

[57] ABSTRACT

Compounds of the structure

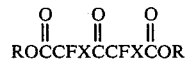

wherein X is —F or Cl and each R is independently —H, —CH$_3$, —C$_2$H$_5$, —CH$_2$CH$_2$CH$_3$, —CH$_2$CH$_2$CH$_2$CH$_3$ or M where M is an alkali metal, an alkaline earth metal, ammonium or a quaternary ammonium are disclosed. The above compounds are prepared by treating a compound of the structure

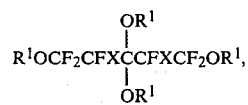

where each R$^1$ is independently —CH$_3$, —C$_2$H$_5$, —CH$_2$CH$_2$CH$_3$ or —CH$_2$CH$_2$CH$_2$CH$_3$; or

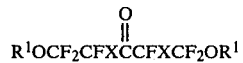

with a strong protic acid, followed, as desired, by base hydrolysis to form carboxylate salts (R=M).

8 Claims, No Drawings

CARBOXYLIC ACIDS, ESTERS AND SALTS OF POLYFLUOROACETONE

BACKGROUND OF THE INVENTION

1. Field of the Invention

This invention relates to carboxylic acids, esters and salts of polyfluoroacetone, processes for their preparation, and monomers and copolymers prepared therefrom.

2. Relation to the Prior Art

U.S. Pat. No. 2,988,537 issued June 13, 1961 to D. W. Wiley, discloses $CH_3OCF_2CF_2COCF_2CF_2OCH_3$ and the process for preparation of $CH_3OCF_2CF_2CO_2CH_3$.

SUMMARY OF THE INVENTION

The present invention provides polyfluorinated, difunctional ketones of formula $\underline{1}$ prepared from either intermediate $\underline{2}$ or $\underline{3}$ by acid-catalyzed hydrolysis

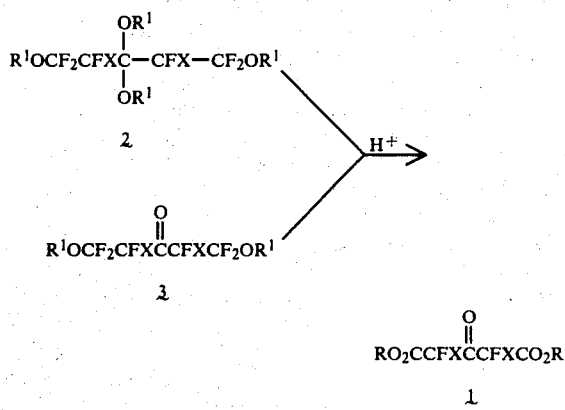

wherein each R is independently —H, —$CH_3$, —$C_2H_5$, —$CH_2CH_2CH_3$, —$CH_2CH_2CH_2CH_3$; each $R^1$ is independently —$CH_3$, —$C_2H_5$, —$CH_2CH_2CH_3$, —$CH_2CH_2CH_2CH_3$; X is —F or —Cl.

Also provided are base-hydrolyzed products of $\underline{1}$ wherein R is M, where M is an alkali metal, alkaline earth metal, ammonium, or quaternary ammonium, and 1,3,3,5-tetraalkoxy polyfluoropentanes of formula $\underline{2}$ useful for preparing the ketones of formula $\underline{1}$.

Ketones provided by this invention are useful for preparing polyfluorinated monomers such as

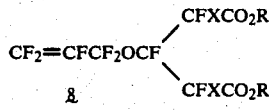

from which water-wettable, dyeable and electrically conductive copolymers can be prepared.

DETAILS OF THE INVENTION

Difunctional polyfluorinated ketones of formula $\underline{1}$ are prepared by the hydrolysis of intermediates $\underline{2}$ or $\underline{3}$ in concentrated protic acids such as sulfuric acid. Products represented by formula $\underline{1}$ are new compositions of matter which can be converted into useful difunctional comonomers. Tetraalkoxy compounds of formula $\underline{2}$ also are new compositions useful as intermediates for the preparation of formula $\underline{1}$ compounds.

Bis(2-alkoxytetrafluoroethyl)ketones ($\underline{3}$) are readily prepared by co-reaction of perhalogenated ethylene, sodium alkoxide and dialkylcarbonate as described in U.S. Pat. No. 2,988,537 (Wiley).

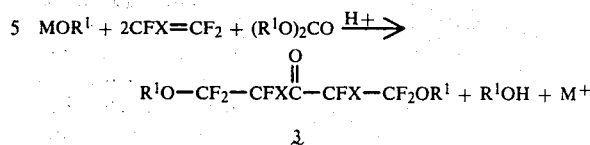

$R^1$ and X are selected from the groups listed above. A novel extension of this reaction in which an alkylating agent such as a dialkyl sulfate is added directly to the reaction mixture, provides 1,3,3,5-tetraalkoxypolyfluoropentanes of formula $\underline{2}$; thus

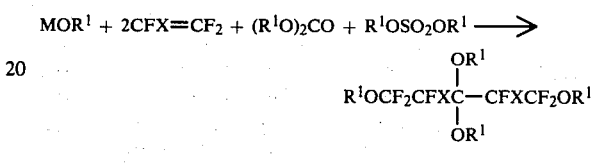

where $R^1$ and X are defined as above. Although the synthesis of intermediate $\underline{2}$ requires an additional reactant, only one reaction step is involved in the preparation of $\underline{2}$ or $\underline{3}$. Yields of dialkyl tetrafluoroacetone-1,3-dicarboxylate ($\underline{1}$) by the hydrolysis of either intermediate $\underline{2}$ or $\underline{3}$ are similar.

In preparing 1,3,3,5-tetraalkoxypolyfluoropentane ($\underline{2}$), conditions described by Wiley in U.S. Pat. No. 2,988,537 for the synthesis of bis(2-alkoxypolyfluoroethyl)ketones ($\underline{3}$) are followed essentially to the point of formation of an intermediate polyfluoroalkoxide, thus:

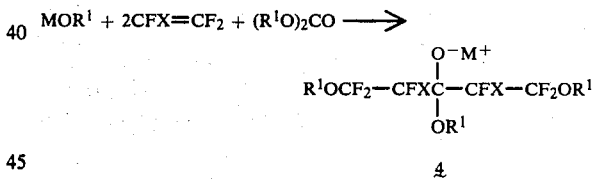

Whereas Wiley teaches acid-catalyzed hydrolysis of $\underline{4}$ to yield the ketone, $\underline{3}$, in the present invention as alkylating agent is introduced which converts the alkoxide anion of $\underline{4}$ to a tetraether; e.g.

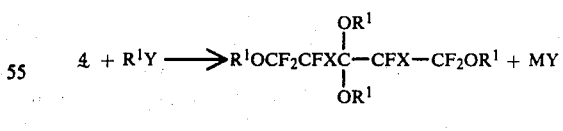

where Y is a radical such as —$OSO_2OR^1$, I—, —$OSO_2F$, or $ArOSO_2O$— wherein Ar is an aromatic radical such as phenyl.

The above alkylation reaction is related to the well-known Williamson synthesis of ethers from alkali metal alkoxides, e.g., $RONa+R^1X\rightarrow ROR^1+NaX$.

Preparation of compounds $\underline{2}$ and $\underline{3}$ requires the addition of tetrafluoroethylene or chlorotrifluoroethylene to an admixture of an alkali metal alkoxide and a dialkyl carbonate in a dry (moisture-free), inert solvent such as tetrahydrofuran, diethyl ether, 1,2-dimethoxy ethane and the like. While other alkali metals, lithium, potassium and cesium, are considered functional equivalents, sodium is preferred because of its availability and relatively low cost. Suitable alkoxides are those of straight chain aliphatic alcohols of up to seven carbon atoms, and particularly useful are the alkoxides of shorter chain alkanols of from 1 to 4 carbon atoms. Methanol, ethanol, n-propanol and n-butanol are illustrative of such alcohols.

The alkali metal alkoxide is used in amount which is at least equimolar to the carbonate ester. Use of larger amounts offers no advantage.

Carbonate esters useful in the synthesis of compounds $\underline{2}$ and $\underline{3}$ are those of straight chain aliphatic alcohols of up to seven carbon atoms, preferably those of alkanols of from 1 to 4 carbon atoms. Since carbonate esters correspond to the structure R'OCOR" in which alkyl groups R' and R" may be independently selected from $-CH_3$, $-C_2H_5$, $-CH_2CH_2CH_3$, $-CH_2CH_2CH_2CH_3$, etc., R' and R" may be the same or different (mixed esters). Normally in the practice of the present invention R' and R" are the same; most useful are $-CH_3$ and $-C_2H_5$.

In the preparation of 1,3,3,5-tetraalkoxypolyfluoropentane ($\underline{2}$) two moles of polyfluoroolefin per mole of metal alkoxide are added to the agitated mixture of alkoxide, carbonate ester and inert solvent. Temperature is maintained below 80° C., generally in the range of 25°–60° C. for 0.5 to 5 hours, normally about 1 hour, until consumption of fluoroolefin is complete. An alkylating agent, such as a dialkyl ester of sulfuric acid, monoalkyl ester of an aryl sulfonic acid or fluorosulfonic acid, or an alkyl iodide is then added directly to the reaction mixture and the same reaction temperature is maintained for 5 to 25 hours, preferably 12–18 hours. The 1,3,3,5-tetraalkoxy polyfluoropentane product is recovered by fractional distillation (Example 2). Useful alkylating agents are those containing straight chain alkyl groups with from one to four carbon atoms, preferably one or two carbon atoms, i.e., $-CH_3$ or $-C_2H_5$. It should be noted that in the overall equation for the synthesis of $\underline{2}$:

$$MOR^1 + 2CFX = CF_2 + n(R^1O)_2CO + R^1Y \longrightarrow$$

$$R^1OCF_2CFX-\underset{\underset{OR^1}{|}}{\overset{\overset{OR^1}{|}}{C}}-CFX-CF_2OR^1 + MY$$

$$\underline{2}$$

$R^1$ may be the same or different. In the latter case, "mixed" ethers are produced which may have special properties related to differences in size, shape and reactivity of the ether groups.

Bis(2-alkoxypolyfluoroethyl)ketones ($\underline{3}$) are prepared in similar solvents to those useful for the synthesis of compounds $\underline{2}$. Two moles of polyfluoroolefin per mole of alkoxide are added to an agitated mixture of alkali metal alkoxide and dialkyl carbonate in an inert solvent and coreacted at temperatures below 80° C., generally in the range 25° to 60° C. The reaction mixture is then acidified and the salt which separates is removed by filtration. Product $\underline{3}$ is recovered from the filtrate by fractional distillation, as described by Wiley (loc. cit.).

The conversion of both intermediates $\underline{2}$ and $\underline{3}$ to dialkyl polyfluoroacetone 1,3-dicarboxylate ($\underline{1}$) is accomplished by contacting the intermediates with strong, protic acids such as concentrated sulfuric acid. The hydrolysis of ROCF$_2$— to

$$ROC-$$

is a known reaction; an example is given by England et al., J. Fluorine Chem. 3, 67 (1973). Generally a mixture of 1–4 parts of concentrated sulfuric acid and 1 part of fluoroether are allowed to react until exothermic reaction is complete and then the product is isolated by distillation.

Compounds represented by formula 1 which are especially useful are those in which each R independently is either H, straight chain alkyl containing 1–4 carbon atoms or M, where M is an alkali metal, alkaline earth metal, ammonium or quaternary ammonium. The metal salts (R=M) which are estensively ionized and soluble in water, are produced from the $C_1$–$C_4$ esters by hydrolysis with alkali metal hydroxides, alkaline earth metal hydroxides, ammonium hydroxide or quaternary ammonium hydroxide. The free dibasic acids (R=H) are readily produced by acid-catalyzed hydrolysis of the diesters in cold water.

The new keto compositions represented by formula $\underline{1}$, wherein each R independently is a straight chain $C_1$–$C_4$ alkyl group, and X is —F or —Cl, are convertible to difunctional monomers by a reaction such as:

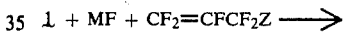

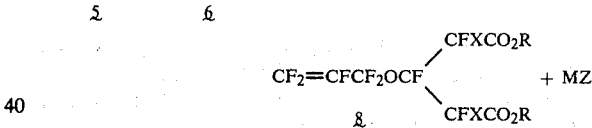

where Z is —OSO$_2$F or —Cl.

The above reaction occurs because the carbonyl group in $\underline{1}$ is a reactive center which adds fluoride derived from the metal fluoride $\underline{5}$ to form a metal polyfluoroalkoxide ($\underline{7}$, below). $\underline{7}$ subsequently forms the polyfluoroallyloxy compound $\underline{8}$ by nucleophilic displacement of the fluorosulfate or chloride group in $\underline{6}$ thus:

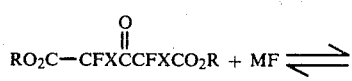

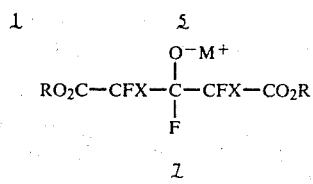

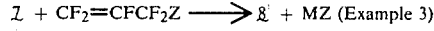

Synthesis is thus a one-vessel sequential addition of reagents $\underline{1}$ and $\underline{6}$ to a suspension or solution of a metal fluoride $\underline{5}$ such as cesium fluoride in a suitable solvent.

Polyfluoroallyl fluorosulfates are the preferred reagents for this displacement, and they can be prepared conveniently by treatment of polyfluoroalkenes with sulfur trioxide, as described in Example 3. Such reactions are typically carried out in sealed Carius tubes at temperatures of 25°–95° C. for periods of 16 hours to 4 days, and the product fluorosulfates are purified by fractional distillation. A preparation of the preferred perfluoroallyl fluorosulfate (pentafluoro-2-propenyl fluorosulfate) is given in Example 3.

The usefulness of intermediate polyfluoroalkoxides such as 7 is determined by their stability, as measured by their ease of thermal decomposition. Because their formation is reversible, the equilibrium concentration of various species in a given reaction mixture are important quantities which determine whether or not the subsequent displacement will occur to form product 8. Solutions in which the equilibrium lies towards the right (high concentration of anion) will be more effective than those in which it lies towards the left (high concentration of carbonyl compound).

The chemistry of metal polyfluoroalkoxides formed by the reaction of certain metal fluorides with polyfluorinated ketones and acid fluorides is known. Published literature on this subject includes: J. A. Young, *Fluorine Chemistry Reviews*, 1, 389 (1967); F. W. Evans, M. H. Litt., A. M. Weidler-Kubanek and F. P. Avonda, *J. Org. Chem.*, 33, 1837; 1839 (1968), and M. A. Redwood and C. J. Willis, *Canad. J. Chem.*, 45, 389 (1967).

Large cations such as $Cs^+$, $K^+$, $Rb^+$ and $R_4N^+$ favor formation of stable polyfluoroalkoxide more than small cations such as $Li^+$ and $Na^+$ because the lattice energy of metallic fluorides is inversely proportional to cation size.

Useful metal fluorides are potassium fluoride (KF), rubidium fluoride (RbF), cesium fluoride (CsF) and tetraalkylammonium fluorides ($R_4^4NF$) such as tetraethylammonium fluoride (($C_2H_5)_4NF$) and tetrabutylammonium fluoride (($C_4H_9)_4NF$). The $R^4$'s may be alike or different, and are alkyls of 1 to 6 carbon atoms, preferably 1 to 4 carbon atoms.

Solvents having a high heat of solution for polyfluoroalkoxides favor formation of 7. Aprotic polar solvents such as N,N-dimethylformamide, acetonitrile, and 1,2-dimethoxyethane are effective for this purpose.

The polyfluoroalkoxide anion is preferably preformed by the addition of the compound 1 to a stirred mixture of the metal fluoride in a suitable aprotic solvent. The completeness of formation of the anion is generally signalled by the extent to which the metal fluoride dissolves in the solvent as the reaction progresses. The stoichiometry of polyfluoroalkoxide anion formation requires one molar equivalent of metal fluoride for each carbonyl group which is converted to its anion, e.g.:

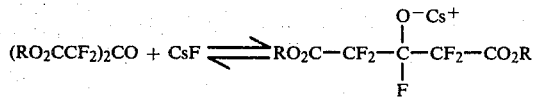

The presence of up to a twice-molar excess of metal fluoride is generally not detrimental.

Formation of polyfluoroalkoxides is usually accomplished at temperatures between −20° C. and +60° C., preferably with external cooling to maintain the temperature between 0° C. and 10° C. The time required to complete polyfluoroalkoxide formation is preferably from 0.5 to 2 hours.

N,N-Dimethylformamide (DMF), acetonitrile, N,N-dimethylacetamide (DMAC), γ-butyrolactone, 1,2-dimethoxyethane (glyme), 1-(2-methoxyethoxy)-2-methoxyethane (diglyme), 2,5,8,11-tetraoxadodecane (triglyme), dioxane, sulfolane, nitrobenzene and benzonitrile are suitable, illustrative aprotic polar solvents for the preparation of polyfluoroalkoxides and their subsequent reaction with the polyfluoroallyl chloride or fluorosulfate. DMF, diglyme, triglyme and acetonitrile are preferred solvents for these reactions.

The apparatus, reactants and solvents should be adequately dried for use in the process of the invention because the presence of water hydrolyzes polyfluoroalkoxides:

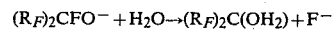

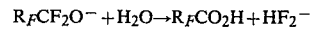

The stoichiometry of the displacement with polyfluoroalkyl chloride or fluorosulfate requires one molar equivalent of this reagent per reactive center in the polyfluoroalkoxide anion, thus:

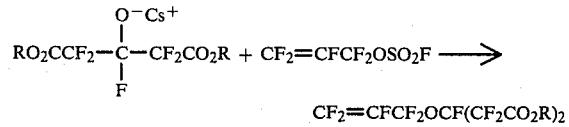

The formation of the polyfluoroalkoxide and its subsequent reaction with the polyfluoroallyl chloride or fluorosulfate can be carried out sequentially without isolation of intermediates in glass apparatus at atmospheric pressure using the normal precautions to exclude moisture. The use of cooling baths and low temperature condensers (e.g. those packed with dry ice and acetone mixtures) serves to moderate the reaction and facilitate the retention of volatile reagents and products. The progress of the displacement reaction is conveniently followed by the appearance of a precipitate of the salt MZ (9), by gas liquid partition chromatography (glpc) and by fluorine nuclear magnetic resonance spectroscopy ($^{19}$F NMR).

The displacement reaction can be carried out between −20° C. and +80° C., and is preferably between 0° C. and 30° C. Typically, the reaction mixture is cooled externally to 0° C. to 15° C. during the addition of the polyfluoroallyl chloride or fluorosulfate, and is then allowed to warm up to 25° C. to 30° C. for the remainder of the reaction time.

The time required to complete the displacement reaction varies from one to 24 hours, and is preferably from 2 to 4 hours. Typically, the reaction mixture is externally cooled for 5 to 45 minutes while the polyfluoroallyl chloride or fluorosulfate is being added, and is then stirred at room temperature for 2 to 3 hours.

The reaction products are isolated by standard procedures. For example, the reaction mixture is poured into five to ten times its volume of water; the insoluble lower layer of fluorinated product is separated, washed free of solvent with more water, dried, and fractionally distilled from phosphorus pentoxide or concentrated sulfuric acid.

The polyfluoroallyloxy compounds (8) are unsaturated monomers which can be converted to new and useful polymers. The monomers can be homopolymerized under high pressure to oligomeric compositions of matter. The economic factors of a costly monomer and the necessity for high pressure operation, however, make it preferable to incorporate these monomers into copolymers formed with less expensive ethylenically unsaturated monomers, e.g., olefins such as ethylene or propylene; halogenated olefins such as tetrafluoroethylene, chlorotrifluoroethylene, trifluoroethylene, vinylidene fluoride, trifluoromethyl trifluorovinyl ether and hexafluoropropylene.

Copolymers which contain from about 5–55 weight percent (about 1–25 mole percent) of polyfluoroallyloxy comonomer have lower melting points than the corresponding polyfluoroolefins, and consequently are more readily molded and shaped into useful objects. Copolymers which contain from about 0.1–10 weight percent, preferably about 1–10 percent (about 0.3–5 mole percent) of a polyfluoroallyloxy comonomer with pendant $CO_2R$ groups can be partially, or essentially completely, hydrolyzed to a copolymer bearing $CO_2H$ groups which have an affinity for cationic dye molecules, or ionized forms thereof; e.g. $CO^-_2M^+$ (M is an alkali metal, alkaline earth metal, ammonium or quaternary ammonium), which imparts electrical conducting properties to the polymer. Such copolymers, when molded into films, are particularly useful as conductive membranes in chlor-alkali electrolytic cells.

SPECIFIC EMBODIMENTS OF THE INVENTION

The following illustrative examples demonstrate ways of carrying out the invention. All parts and percentages are by weight unless otherwise stated. For structure confirmation analyses, fluorine nuclear magnetic resonance chemical shifts are in parts per million from internal fluorotrichloromethane, and proton nuclear magnetic resonance chemical shifts are in parts per million from internal tetramethylsilane. Infrared and nuclear magnetic resonance spectra were recorded on undiluted liquid samples unless otherwise stated.

EXAMPLE 1

Dimethyl Tetrafluoroacetone-1,3-dicarboxylates

A. Bis(2-Methoxytetrafluoroethyl)Ketone

Preparation as described by D. W. Wiley, U.S. Pat. No. 2,988,537 (1961).

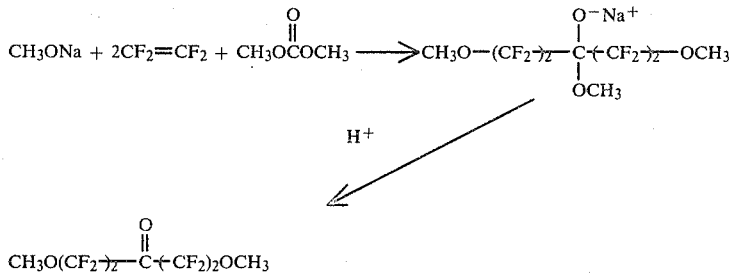

A mixture of 10.8 parts of sodium methoxide and 60 parts of dimethyl carbonate (B.P. 90°–91° C.) was placed in a 400-ml reactor fitted with a thermocouple well and inlet tube. After evacuating and flushing with tetrafluoroethylene, agitation was started and tetrafluoroethylene was added at a rate such as to maintain the temperature at 40° C. During the first hour of addition, the pressure was below atmospheric but slowly rose to 40 lb/sq. in. after 2 hours. After 4 hours at 40 lb/sq. in, there was no more uptake of tetrafluoroethylene, and the temperature dropped to that of the room. During this time 41 parts of tetrafluoroethylene were absorbed (100% of theory).

The resulting thick slurry was taken up in ether and treated with 20 parts of 100% sulfuric acid with stirring and cooling. The precipitated sodium bisulfate was removed by filtration and thoroughly washed with ether. The combined etheral filtrates were treated with 5 parts of sodium fluoride to remove trace amounts of hydrogen fluoride and then concentrated. Distillation through a spinning-band column at 47 mm. Hg yielded, after a forerun of methyl alcohol and dimethyl carbonate, 48 parts of sweet-smelling oil; B.P. 68°–80° C. at 47 mm Hg. Careful fractionation through a 30-inch packed column at 11 mm Hg pressure yielded (1) 6.4 parts (17% of theory) of methyl β-methoxytetrafluoropropionate, B.P. 40°–41° C. at 11 mm Hg, $n_D^{25}$ 1.3358; (2) 3.2 parts intermediate fraction B.P. 41°–48° C.; and (3) 43.9 parts (75% of theory) of bis(2-methoxytetrafluoroethyl)ketone, B.P. 48° C. at 11 mm Hg, $n_D^{25}$ 1.3168, $d_{25}^{25}$ 1.477. Total yield of ester and ketone based on sodium methoxide was 92%. Both n-m-r and infrared spectra were in agreement with these structures.

Analysis Calcd. for $C_5H_6F_4O_3$: C, 31.6; H, 3.2; F, 30.0; N.E., 190. Found: C, 31.8; H, 3.3; F, 39.7; N.E. 182.

Analysis Calcd. for $C_7H_6F_8O_3$: C, 29.0; H, 2.1; F, 52.4; N.E. 290. Found: C, 29.1, H, 2.3; F, 52.4; N.E. 270.

B. Dimethyl Tetrafluoroacetone-1,3-dicarboxylate from Bis(2-methoxytetrafluoroethyl) Ketone

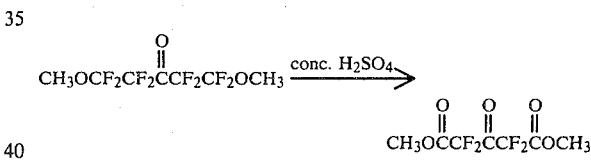

To 124.4 g of bis(2-methoxytetrafluoroethyl)ketone was added dropwise 125 ml concentrated $H_2SO_4$. The reaction mixture was heated at 60°–70° C. (50 mm Hg) for 16 hours. All volatiles were removed by heating up to 100° C. at 0.5–1.0 mm Hg and collected in a −78° C. trap. The crude distillate was distilled to give 74 g (61.5%) of the product, bp 56° C. (1.2 mm Hg). The structure was confirmed by $^1H$ nmr and $^{19}F$ nmr.

EXAMPLE 2

Dimethyl Tetrafluoroacetone-1,3-dicarboxylate

A. 1,3,3,5-Tetramethoxyoctafluoropentane

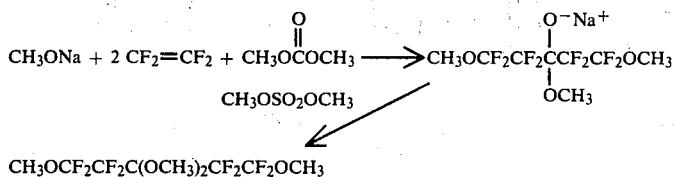

A mixture of 27.0 g (0.50 mol) of sodium methoxide 56.0 g (0.62 mol) of dimethyl carbonate, and 100 ml of dry tetrahydrofuran was agitated in a 350 ml tube under 1-3 atm of tetrafluoroethylene. Tetrafluoroethylene was pressured in as consumed until 110 g (1.1 mol) had been added. The mildly exothermic reaction kept the temperature near 35° C.; after the addition, the reaction mixture was heated at 40° C. for 1 hr. The viscous solution from this reaction was treated directly with 75.6 g (0.60 mol) of dimethyl sulfate at 40° C. for 15 hr. Filtration and distillation afforded 87.6 g (52%) of 1,3,3,5-tetramethoxyoctafluoropentane, bp 54° C. (0.3 mm Hg), $n_D^{24}$ 1.3605, whose structure was confirmed by Ir 3.29, 3.33, and 3.42 (satd CH) 8–9μ (CF, COC). Nmr (CCl$_4$) 'H$_{19}$δ3.68 (s, 1, CF$_2$OCH$_3$) and 3.57 (p, $J_{HF}$ 1.3 Hz, 1, C (OCH$_3$)$_2$); $^{19}$F −88.2 (m, 1, CR$_2$O) and −116.5 ppm (m, I, CF$_2$).

Anal. Calcd. for C$_9$H$_{12}$F$_8$O$_4$: C, 32.16; H, 3.60; F, 45.21. Found: C, 32,57; H, 3.72; F, 44.61.

B. Dimethyl Tetrafluoroacetone-1,3-dicarboxylate

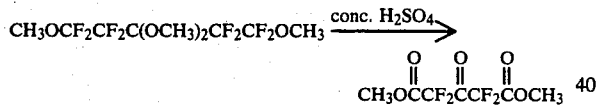

To 50 ml of conc. H$_2$SO$_4$ was added dropwise 33.6 g (0.10 mol) of 1,3,3,5-tetramethoxyoctafluoropentane. After the mildly exothermic reaction had subsided, the mixture was heated at 70° C. (50 mm Hg) to remove volatiles and then distilled at ca. 50° C. (1 mm Hg). The crude distillate was then fractionated to afford 16.9 g (69%) of dimethyl tetrafluoroacetone-1,3-dicarboxylate, bp 58° C. (2 mm Hg), $n_D^{22}$ 1.3713. Structure was confirmed Ir 3.28, 3.34 and 3.48 (satd CH), 5.57 (C═O) 5.64 (sh—C═O), 8–9μ (CF, COC) Nmr (CCl$_4$) 'Hδ4.00 (s, OCH$_3$); $^{19}$F-113 ppm (s, CF$_2$).

Anal. Calcd. for C$_7$H$_6$F$_4$O$_5$: C, 34.16; H, 2.46; F, 30.88; mol wt. 246. Found: C, 34.18; H, 2.66; F, 30.95; mol wt. 246. (mass spec).

The same reaction on a 0.56 mole scale gave the diester in 82% yield.

EXAMPLE 3

Dimethyl Perfluoro-3-allyloxyglutarate

A. Pentafluoro-2-propenyl fluorosulfate (Perfluoroallyl fluorosulfate)

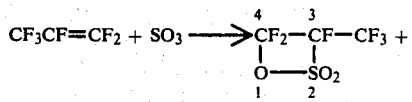

$$CF_2\!=\!CF\!-\!CF_2OSO_2F$$

A mixture of commercial liquid sulfur trioxide (10 ml) and hexafluoropropene (45 g, 0.30 mol) was sealed in a Carius tube at liquid nitrogen temperature, mixed well at 25° C., allowed to stand for 4 days at 25° C., and finally heated in a steam bath for 6 hours. From two such tubes, there was obtained by distillation, 3-(trifluoromethyl)-3,4,4-trifluoro-1-oxa-2-thiacyclobutane 2,2-dioxide (2-hydroxy-1-trifluoromethyl-1,2,2-trifluoroethane sulfonic acid sultone, D. C. England, M. A. Dietrich and R. V. Lindsey, Jr., J. Amer. Chem. Soc., 82, 6181 (1960)) (25 g, 22%) bp 44° C., and pentafluoro-2-propenyl fluorosulfate (hereinafter referred to as perfluoroallyl fluorosulfate) (73 g, 63%), bp 58°–60° C.

Perfluoroallyl fluorosulfate is characterized by: $\lambda_{max}$ 5.55 (C═C) and 6.75 μm (SO$_2$); $^{19}$F NMR, 46.1 (t J=8.5 Hz, each member d J=1.8 Hz) 1F, SO$_2$F, −74.0 (d J=28.2 Hz, each member d J=13.9 Hz, d J=8.5 Hz, d J=7.8 Hz) 2F, −91.2 (d J=50 Hz, each member d J=40.5 Hz, t J=7.8 Hz) 1F, −104.7 (d J=119.4 Hz, each member d J=50 Hz, d J =28.2 Hz) 1F, and −192.4 ppm (d J=119.4 Hz, each member d J=40.5 Hz, t J=13.9 Hz, d J=1.8 Hz) 1F.

B. Dimethyl Perfluoro-3-alloxyglutarate

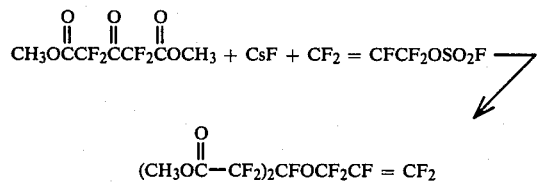

To 27.3 g (0.18 mol) dry CsF in 100 ml diglyme was added 43.5 g (0.18 mol) 0═C(CF$_2$COOCH$_3$)$_2$ (Examples 1, 2) at 5°–10° C. and stirred for 1 hr; 41.4 g (0.18 mol) CF$_2$═CFCF$_2$OSO$_2$F was added at 5°–10° C. and the mixture was stirred further for 3 hours. The reaction mixture was thrown into 1 liter of H$_2$O and the lower layer separated. This was washed twice with H$_2$O. After treatment with 20 ml H$_2$SO$_4$ at 0° C. and extraction with CFCl$_2$CF$_2$Cl, the extract was distilled in a molecular still to give 4.54 g (7.2% yield) of product, bp=51°–53° C. (0.1 mm Hg). Structure was confirmed by $^{19}$F nmr (F11): −68.48 ppm (OCF$_2$CF═); −93.45 ppm cis-(CF═CFF); −105.91 ppm trans-(CF═CF); −117.10 ppm (CF$_2$COOCH$_3$); −142.78 ppm (CF$_2$CF$_2$OCF═); −190.35 ppm (CF═CF$_2$). 'H nmr (F11/TMS): 3.96 (singlet, CH$_3$). Ir (neat): 3.37μ, 3.49μ (sat CH); 5.60 2 (>C═0, CF$_2$═CF); 8–10μ (CF,CO).

Anal. Calcd. for C$_{10}$H$_{10}$H$_6$O$_5$: C, 30.32; F, 47.96; H, 1.53. Found: C, 30.45; F, 48.10; H, 1.48.

I claim:

1. Compounds of the structure $$\text{ROCCFXCCFXCOR}\ \overset{O\ \ O\ \ O}{\|\ \ \|\ \ \|}$$

wherein X is —F or —Cl and each R is independently —H, —CH$_3$, —C$_2$H$_5$, —CH$_2$CH$_2$CH$_3$, —CH$_2$CH$_2$CH$_2$CH$_3$ or M where M is an alkali metal, an alkaline earth metal, ammonium or quaternary ammonium.

2. The compounds of claim 1 wherein X is —F.

3. The compounds of claim 2 wherein both R's are —CH$_3$.

4. The compounds of claim 2 wherein both R's are —C$_2$H$_5$.

5. A process of preparing compounds of the structure $$\text{ROCCFXCCFXCOR}\ \overset{O\ \ O\ \ O}{\|\ \ \|\ \ \|}$$

wherein X is —F or —Cl and each R is independently —CH$_3$, —C$_2$H$_5$, —CH$_2$CH$_2$CH$_3$ or —CH$_2$CH$_2$CH$_2$CH$_3$ by treating a compound of the structure $$\text{R}^1\text{OCF}_2\text{CFXCCFXCF}_2\text{OR}^1\ \overset{\overset{\displaystyle OR^1}{|}}{\underset{\displaystyle OR^1}{|}}$$

wherein each R$^1$ is independently —CH$_3$, —C$_2$H$_5$, —CH$_2$CH$_2$CH$_3$, or —CH$_2$CH$_2$CH$_2$CH$_3$ with a strong protic acid.

6. The process of claim 5 wherein X is —F.

7. The process of claim 6 wherein the R$^1$'s are —CH$_3$.

8. The process of claim 6 wherein the R$^1$'s are —C$_2$H$_5$.

* * * * *